United States Patent [19]

Hanaway et al.

[11] Patent Number: 5,000,921
[45] Date of Patent: Mar. 19, 1991

[54] MULTIPLE PIPETTE SAMPLES

[76] Inventors: Richard W. Hanaway, 906 Carol Ann Ct., Roseville, Calif. 95678; James Hrudicka, Star Rte. 89031, Box 3120, Las Vegas, Nev.

[21] Appl. No.: 490,162

[22] Filed: Feb. 8, 1990

Related U.S. Application Data

[63] Continuation of Ser. No. 923,117, Oct. 24, 1986, abandoned.

[51] Int. Cl.$^5$ ............................................. B01L 3/02
[52] U.S. Cl. .............................. 422/100; 73/863.32; 73/864.11; 73/864.14; 435/301
[58] Field of Search ................ 422/100; 73/863.32, 73/864.11, 864.14; 435/301

[56] References Cited

U.S. PATENT DOCUMENTS

4,511,534 4/1985 Bennett, Jr. et al. ............... 422/100
4,565,100 1/1986 Malinoff ........................... 422/100 X

*Primary Examiner*—Robert J. Warden
*Assistant Examiner*—Jill Johnston
*Attorney, Agent, or Firm*—Jerry T. Kearns

[57] ABSTRACT

A pipette sampling device for removing and transferring a plurality of liquid samples consists of an improved structure which allows a low cost manufacturing process, the use of a minimum amount of material in such process, and a pipette cavity shaped such that hydraulic principles insure accuracy during filling and dispensing. The pipette sampling device is positionable within a filling tray which permits an initial filling of the pipettes by a liquid through capillary action, and an actuating device is then attached over the pipettes. The actuating device provides a vacuum so that the liquid is drawn into each pipette cavity until the walls and rims of all of the cavities are completely wetted and a stretched meniscus is formed at the top of each cavity. The actuator may then be utilized to effect the dispensing of the liquid in each pipette cavity through a provided pressure. To accomplish this process, the sampling device is constructed to include a manifold which is designed as an inflexible, rigid monocoque structure.

23 Claims, 5 Drawing Sheets

MULTIPLE PIPETTE SAMPLES

CROSS REFERENCE TO RELATED APPLICATIONS

This application is a continuation of application Ser. No. 923,117, filed on 10/24/86, now abandoned.

BACKGROUND OF THE INVENTION

1. Background of the Invention

The present invention relates to the field of fluid handling, and more particularly pertains to an improved multiple pipette sampler system and related apparatus.

2. Description of the Prior Art

Pipettes of various configurations for withdrawing measured liquid samples from one container and transferring them to a second container have long been in use and are recognized as prior art. Typically, these pipettes require time-consuming care in achieving accurate measurement, and in their cleaning or sterilization between respective uses. Inaccuracies in measurements stem from lack of positive control of the shape and position of the liquid at the top and tip of the pipette at the time of filling, and also from variations in the amount of liquid left in the pipette tip upon expelling. Attempts to control these inaccuracies have in the past taken the form of costly manufacturing methods and the use of additional parts to control the filled liquid position, as well as the use of elaborate apparatuses to encourage uniform dispensing.

Advances in microbiological, immunological, and other statistical research methods have made individual sampling impractical in terms of time and cost. The requirement for large numbers of samplings of contaminating liquids has created a need for low cost, disposable, multiple pipette samplers. The prior art reveals a number of devices which represent attempts to solve the above-identified problems, and several multiple sample pipette assemblies are also in existence. Some of these devices are shown in U.S. Pat. Nos. 3,261,208, 3,568,735, 4,158,035, 4,461,328 and 4,468,974. A review of these patents will reveal that the attempts to provide accurate, multiple samples involve increased precision, materials, of numbers of parts—all of which add to the manufacturing cost and complexities. As such, it can be appreciated that the prior art attempts to control the uniformity of operation have resulted in awkward and time-consuming procedures and hardware.

As such, it appears that there is a continuing need for a multiple pipette sampler system which provides for a fast, convenient transfer of multiple liquid samples in repetitive situations wherein the construction thereof permits accurate sampling and minimum manufacturing cost, preferably in a disposable unit. In this respect, the present invention substantially fulfills this need.

SUMMARY OF THE INVENTION

In view of the foregoing disadvantages inherent in the known types of multiple pipette sampler systems now present in the prior art, the present invention provides an improved multiple pipette sampler system which permits an extremely accurate measuring of the quantity of liquid drawn into and dispensed from a plurality of pipette cavities. As such, the general purpose of the present invention, which will be described subsequently in greater detail, is to provide a new and improved multiple pipette sampler which has all the advantages of the prior art multiple pipette samplers and none of the disadvantages.

To attain this and in order to take multiple uniform samples, identical pipette cavities are formed in a thin (0.008 to 0.040 inches) plastic sheet. A second thin plastic sheet is formed so that when joined to the first sheet, a manifold is created whereby equal pressure may be applied to each pipette cavity. At the same time, the joining of the first and second sheets produces a rigid monocoque structure which holds the pipette cavities in a single plane.

In order to obtain uniform initial conditions, a preformed plastic filling tray may be provided so that the level of the liquid sample is identical for each use. When placed in this filling tray, each pipette tip draws in an equal volume of liquid due to capillary action.

A quick release connection is provided in the plastic manifold, whereby a small actuating device is attached to the pipette assembly and is operable as a source of vacuum or pressure. When the actuating device is operated, i.e., when it is utilized to draw a vacuum on the manifold, liquid is drawn into the pipette cavities until they are overfilled to a point where the cavity walls are completely wetted and a convex, stretched meniscus is formed at the top of each cavity. Since the force required to produce this stretched meniscus is large compared to irregularities, such as the levelness of the pipette array or differences in the surface conditions of the plastic, these overfilled liquid volumes are nearly identical. When the actuator is released to a preset stop, identical concave meniscuses are formed in each cavity with equal volumes of liquid then being retained therein. The pipette cavities are formed in the shape of the upper one half of an hourglass which reduces the size of the tips to small capillary tubes upon which no liquid drops are formed when the pipettes are withdrawn from the liquid in the filling tray. Each pipette cavity now holds an equal volume of liquid sample.

The multiple pipette sampler comprising the invention is then transferred to receiving wells, the actuator is released, and the liquid samples are expelled. The pipette tips are placed so that they are below the liquid level in the receiving wells and, when they are withdrawn, capillary action removes all but a small, uniform volume of liquid from each pipette tip.

Since the actuating device is attached to the multiple pipette array during use, whereby it comprises a single unit in combination with the array, the complete device is fully mobile, and is operable to quickly and easily transfer liquid samples in a one-hand operation. After use, the contaminated pipette array and filling tray are discarded, while the actuator is retained for further use.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved multiple pipette sampler assembly which has all the advantages of the prior art multiple pipette sampler assemblies and none of the disadvantages.

It is another object of the present invention to provide a new and improved multiple pipette sampler assembly which may be easily and efficiently manufactured and marketed.

It is a further object of the present invention to provide a new and improved multiple pipette sampler assembly which is of a durable and reliable construction.

An even further object of the present invention is to provide a new and improved multiple pipette sampler assembly which is susceptible of a low cost of manufacture with regard to both materials and labor, and which accordingly is then susceptible of low prices of sale to the consuming public, thereby making such multiple pipette sampler assemblies economically available to the buying public.

Still yet another object of the present invention is to provide a new and improved multiple pipette sampler assembly which provides in the apparatuses and methods of the prior art some of the advantages thereof, while simultaneously overcoming some of the disadvantages normally associated therewith.

Still another object of the present invention is to provide a new and improved multiple pipette sampler assembly which facilitates an extremely accurate measuring of liquid samples contained in each of a plurality of pipette cavities.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

With reference now to the drawings, and in particular to FIGS. 1 through 12 thereof, a new and improved multiple pipette sampler embodying the principles and concepts of the present invention will be described.

Figure 1:
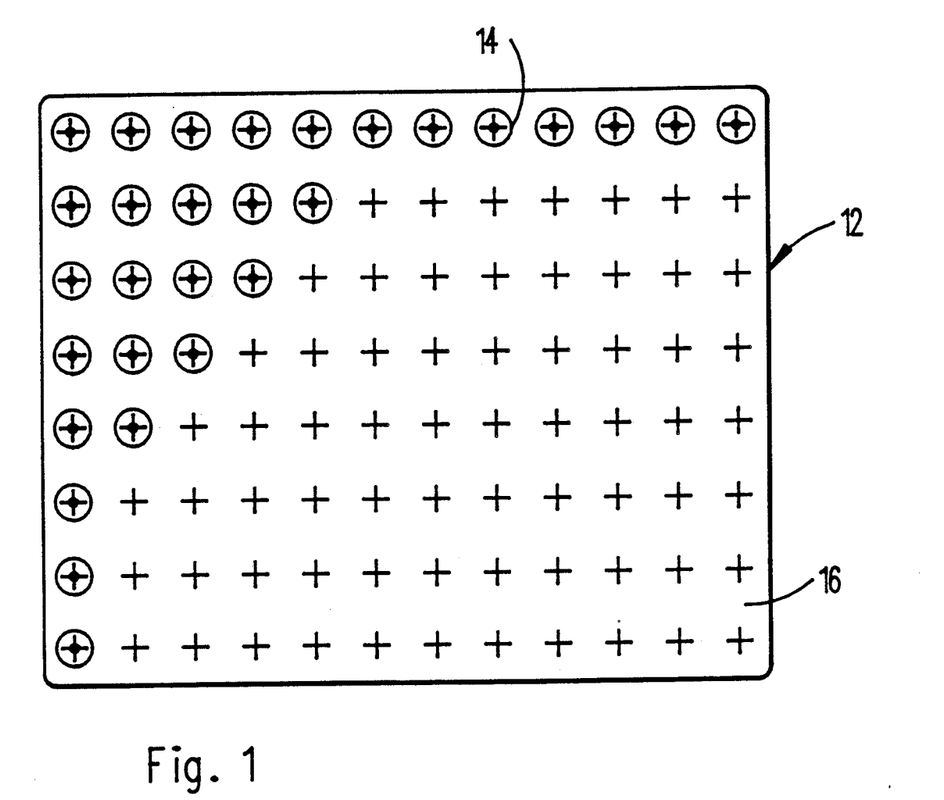
FIG. 1 is a top plan view of the pipettes formed in a pipette sheet comprising a part of the present invention.
Figure 2:
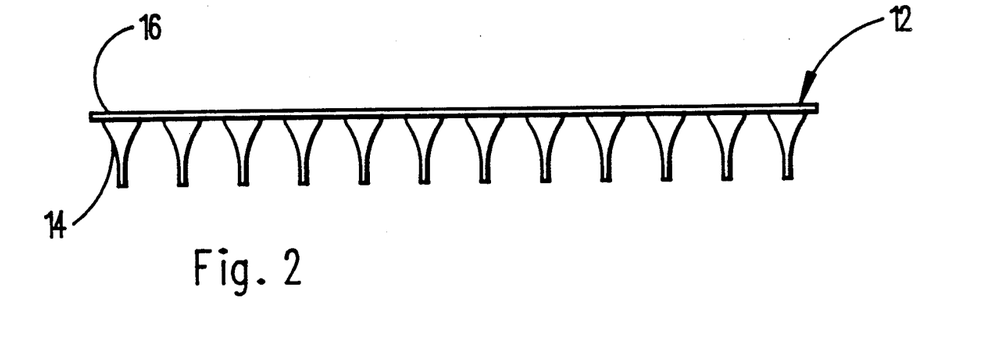
FIG. 2 is a side elevation view of the pipette sheet structure.

As described herein, the multiple pipette sampler device is used to simultaneously rehydrate and innoculate a 96 well microtiter tray. Thus, the pipette sheet 12, as illustrated in FIGS. 1 and 2, is an array of 96 pipette cavities 14 depending downwardly from an integral flat sheet 16. A precision die is used to thermoform a 0.015 to 0.020 inch polyvinylchloride (PVC) plastic sheet so that each cavity 14 is identical. The tip of each pipette cavity 14 is removed so that a liquid may be drawn into the cavity.

Figure 3:
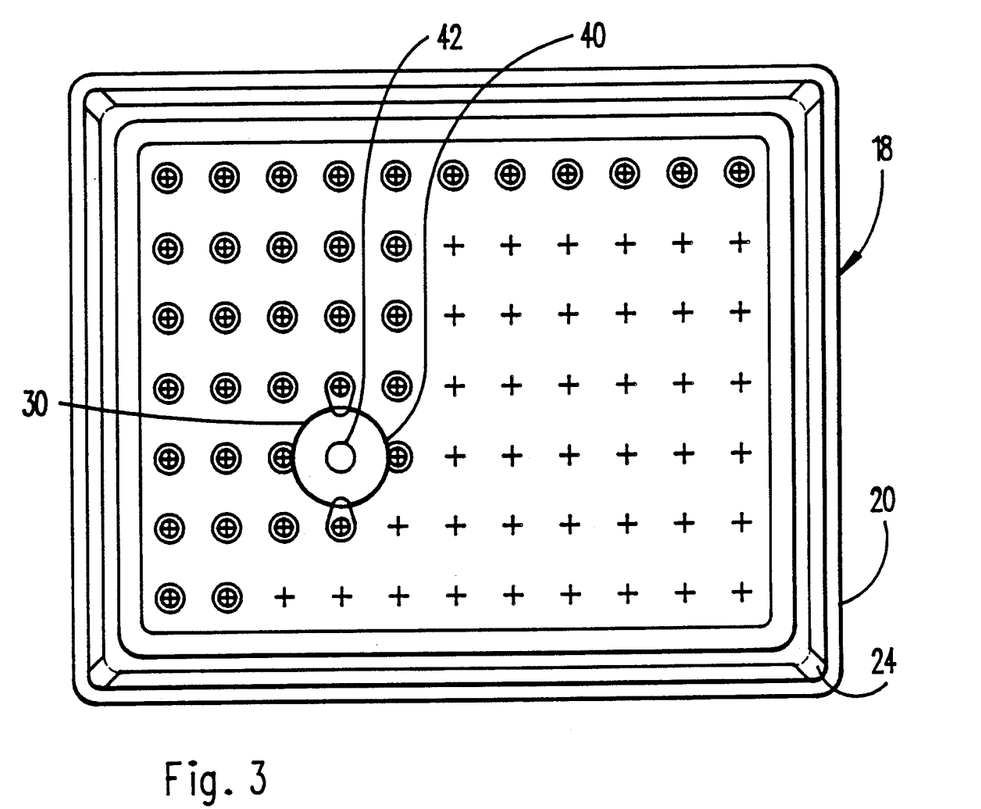
FIG. 3 is a top plan view of the housing forming a part of the present invention.
Figure 4:
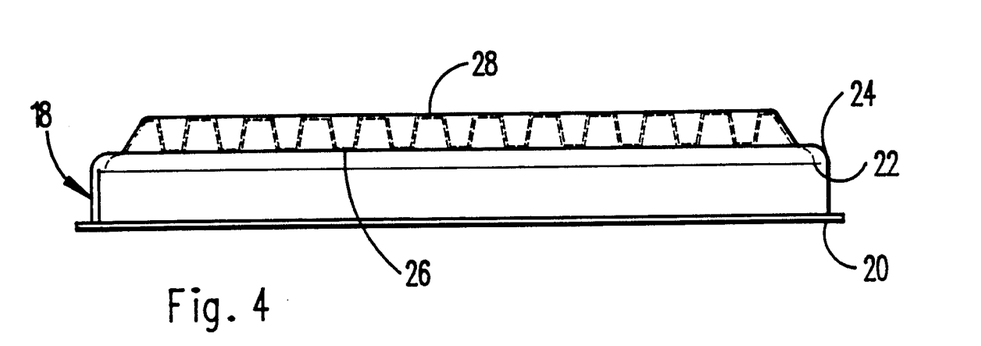
FIG. 4 is a side elevation view of the housing.

In a similar manner, the housing 18, as shown in FIGS. 3 and 4, is thermoformed in a second die from a 0.015 to 0.020 inch polyvinylchloride plastic sheet. The concavely-shaped housing 18 includes a skirt portion 20 and an interiorly formed step 22. Vent passages 24 are formed at each corner of the housing 18, and a plurality of stiffening depressions 26 are thermoformed in a top surface 28 of the housing. As best illustrated in FIG. 3, an actuator attachment 30, which will be subsequently described in greater detail, is also integrally formed or otherwise separately attached to the top surface 28 of the housing 18.

Figure 5:
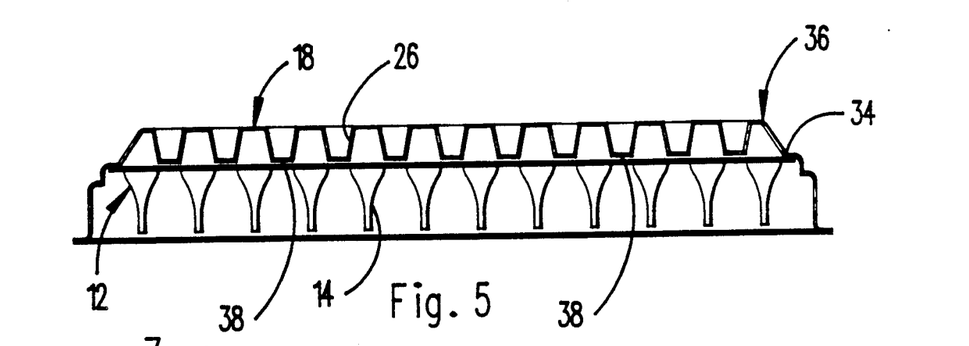
FIG. 5 is a cross-sectional view of the assembled pipette sheet and housing.

The pipette sheet 12 and the housing 18 are joined together, preferably by dielectric heat sealing, into a rigid structure 32 as shown in FIG. 5. In this regard, the pipette sheet 12 and the housing 18 are sealed along a peripheral edge generally designated by the reference numeral 34. This sealing effectively forms a manifold 36, and each of the stiffening depressions 26 are heat welded at bottom sections 38 thereof to the pipette sheet 12, thus to form a beam structure clearly illustrated in the cross-sectional view of FIG. 5. As such, each pipette cavity 14 may have equal vacuum or pressure applied to it, and each such cavity is held in a rigid plane during such pressure variations.

Figure 8:
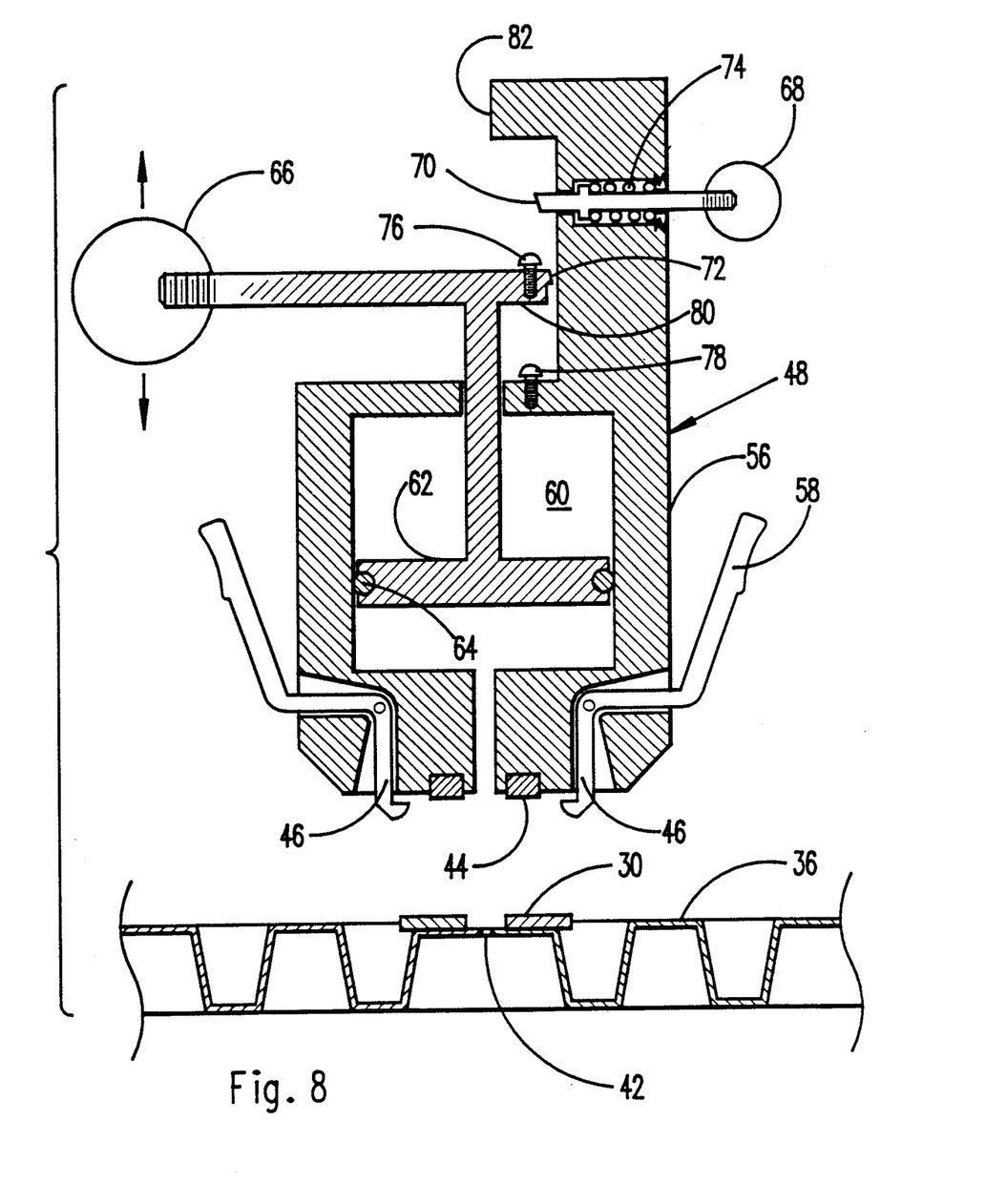
FIG. 8 is a cross-sectional view of the actuator attachment utilizable in the combination of the present invention.

With further reference to the aforementioned actuator attachment 30, as best illustrated in FIGS. 3 and 8, it can be seen that the same consists of a 0.030 inch thick plastic washer which is sealed or otherwise affixed to the housing 18, preferably in a preformed cavity 40. A through-extending aperture or passage 42 is provided into the manifold 36 of the assembly. The washer 30 serves as a sealing surface for a gasket 44 and as purchase for grasping hooks 46 which join an actuator device 48 to the pipetting device 32, thus to form a single portable unit.

Figure 6:
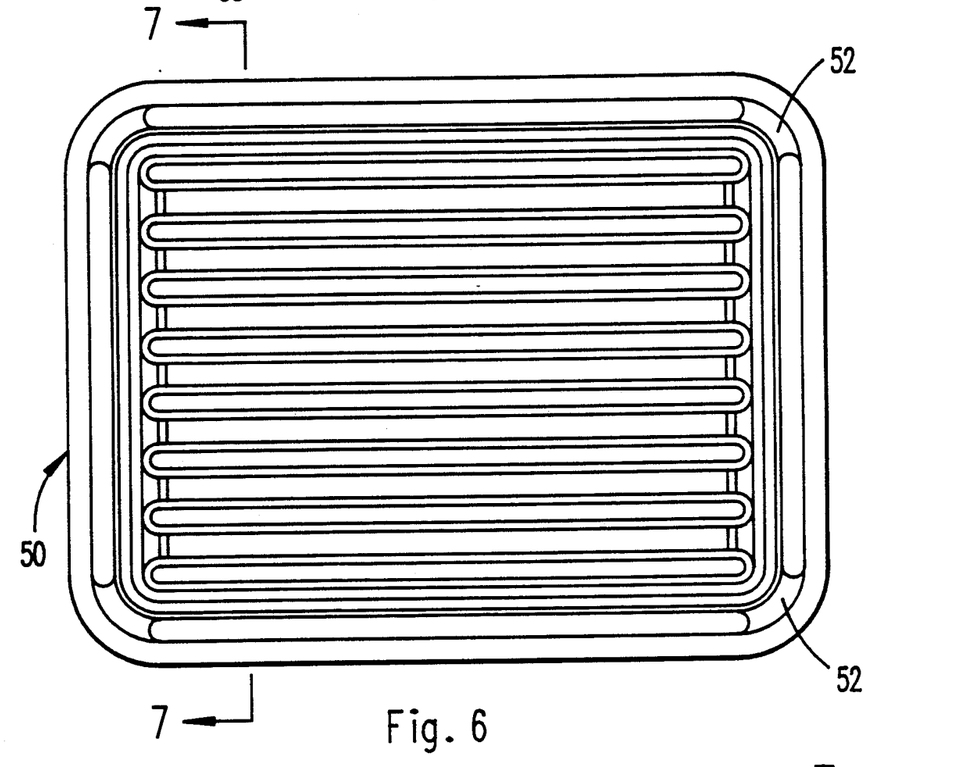
FIG. 6 is a top plan view of the filling tray forming a part of the present invention.
Figure 7:
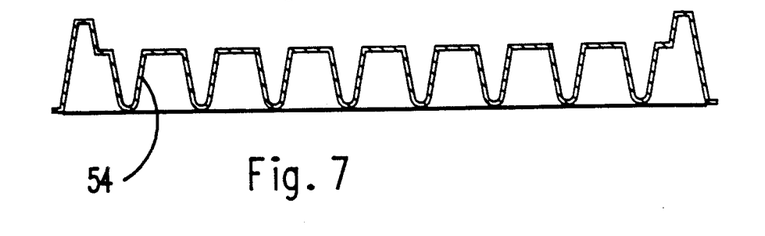
FIG. 7 is a cross-sectional view of the filling tray taken along the line 7—7 in FIG. 6.

A filling tray 50, as shown in FIGS. 6 and 7, is thermoformed in a die from a 0.015 to 0.020 inch plastic sheet. The integral construction of the tray 50 includes vents 52 at the four corners thereof. Additionally, a plurality of liquid holding slots 54 are formed in the tray 50, with these slots being designed to retain a liquid to be drawn into the pipette cavities 14 in a manner yet to be described.

With further reference to the actuator device 48, reference is again made to FIG. 8 of the drawings for a complete description thereof. In this respect, it can be seen that the actuator device 48 includes a housing 56, with the aforementioned grasping hooks 46 being pivotally mounted within the housing. The hooks 46 are provided with upwardly extending, manually movable handles 58, thus to provide for their rapid attachment to and release from the actuator attachment 30. A pressure chamber or cylinder 60 is formed within the housing 56 and includes a reciprocably movable piston 62 mounted therein. The piston 62 is provided with a sealing gasket 64 so as to prevent airflow around the peripheral edges of the piston. A topmost portion of the piston 62 is attached to a manually operable handle 66 which thus facilitates the upward or downward movement of the piston within the chamber 60.

A manually operable, spring-biased filled position catch 68 is reciprocally mounted within the housing 56. The catch 68 includes an extended end portion 70 that includes a cammed surface which slides over an extended edge 72 of the handle 66. The extended edge 72 of the handle 66 is also cammed so that a slidable engagement between the edges 70, 72 is facilitated during an upward movement of the handle 66. After the edge 72 moves past the edge 70, the spring 74 moves the edge 70 beneath the edge 72, thus to maintain the piston 62 in its upwardly directed position.

The actuator device 48 further includes limit stops 76, 78. More specifically, the limit stop 76 comprises a threaded member which may be moved upwardly or downwardly within the handle 66 and is operable to limit the amount of upward movement of the handle relative to the housing 56. In effect, the limit stop 76 comprises an overfill limit stop inasmuch as it can be adjusted to a point where the pipette cavities 14 are precisely filled by an upward movement of the piston 16.

Similarly, the limit stop 78 comprises a threaded member which may be adjusted upwardly or downwardly relative to the housing 56, with this stop comprising a liquid expelling limit stop, whereby a precise dispensing of liquid from the cavities can be achieved by a downward movement of the piston 62 until an abutable relationship between the handle 66 and the limit stop 78 is experienced. The limit stop 78 is abutable with an extended handle portion 80, while the overfill limit stop is abutable with an extended housing portion 82.

OPERATION

Figure 9:
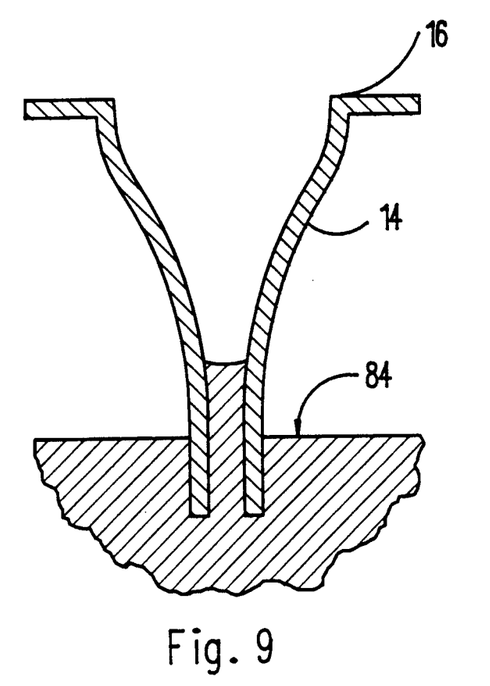
FIG. 9 is a cross-sectional view of a pipette illustrating the same initially inserted into a liquid, whereby capillary action has been initiated to partially fill the pipette.
Figure 10:
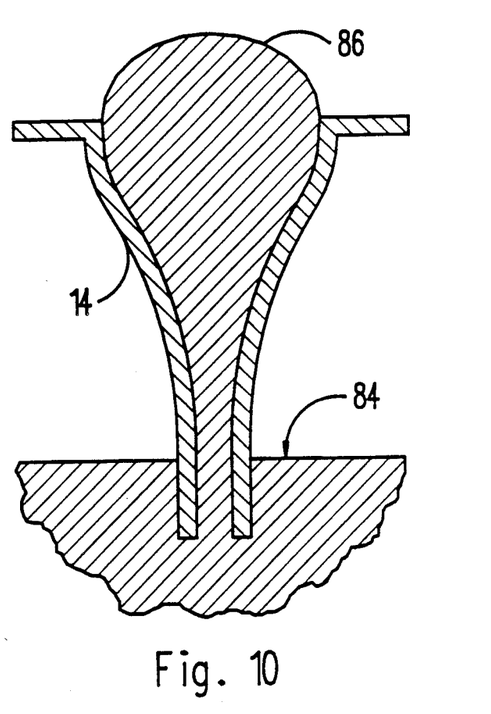
FIG. 10 is a cross-sectional view of the pipette showing the same filled with liquid after a use of the actuator attachment forming a part of the present invention.

In operation, a premeasured volume of innoculating liquid 84, such as shown in FIGS. 9, 10, 11 and 12, is placed in the filling tray 50 illustrated in FIGS. 6 and 7. The pipetting device 32 is then lowered into the filling tray 50, and the pipette tips are filled to equal levels by capillary action as shown in FIG. 9. The actuating device 48, as best illustrated in FIG. 8, is then attached and sealed to the pipetting device 32 by means of the grasping hooks 46 being hooked over the edges of the washer 30. When the piston 62 is drawn upwardly within the housing 56, a vacuum is formed within the lower portion of the pressure chamber 60. As the piston 62 is drawn upwardly until the overflow limit stop 76 abuts with the extended housing edge 82, the innoculating liquid 84 is drawn into each pipette cavity 14 until the walls and rims of all such cavities are completely wetted and a stretched meniscus 86 is formed at the top of each cavity as shown in FIG. 10.

Figure 11:
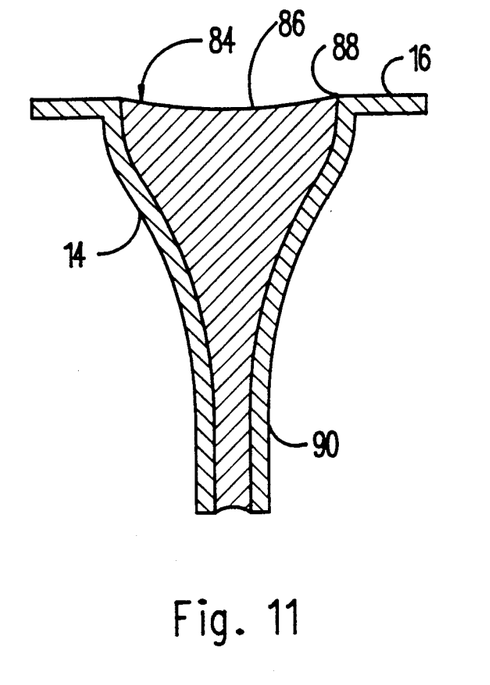
FIG. 11 is a cross-sectional view of a pipette illustrating its filled condition after the partial release, of actuator vacuum.

Since the vacuum required to form a meniscus 86 is relatively large, each meniscus serves to limit and equalize the liquid volumes held in the pipette cavities 14 at this overflow condition, despite small variations due to levelness of the tray 50, impurities, or the wetting of the plastic walls. A manual release of the piston handle 66 will allow the piston 62 to travel partially downwardly within the cylinder 60 until the extended edge 72 engages the edge 70 forming a part of the filled position catch 68. The piston 62 is then locked in this position, while the partial downward movement of the piston 62 results in at least a partial release of vacuum within the manifold 36. As such, predetermined equal liquid volumes are retained in all of the pipette cavities 14, as best illustrated in FIG. 11. At this point, each pipette cavity rim 88 is uniformly wetted, and the meniscus 86 again tends to equalize the liquid volumes.

Figure 12:
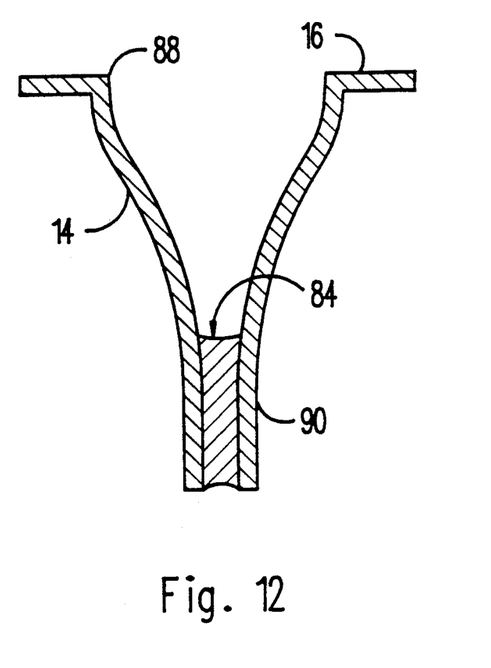
FIG. 12 is a cross-sectional view of the pipette after a dispensing of the fluid contained therein.

The complete unit consisting of the actuating device 48 and the pipetting device 32 is then removed from the filling tray 50 and transferred to an unillustrated 96 well microtiter tray. The housing skirt 20 and the associated step 22, as best illustrated in FIG. 4, position the pipette tips 90 in the receiving wells. The filled position catch 68 may then be manually pulled from the housing 56, thereby to effect a disengagement of the edges 70, 72 so as to release the piston 62 for further downward movement within the cylinder 60. The piston 62 then returns to its original position, and most of the innoculating liquid 84 is expelled from the pipette cavities 14. The pipette tips 90 have been positioned so that at this time, they are below the level of liquid 84 in the microtiter tray wells. The complete unit is then removed from the microtiter tray and surface tension draws the liquid volume in each tip 90 down to an equal level, as illustrated in FIG. 12, thereby to ensure that equal liquid volumes have been delivered to the microtiter tray wells. In this regard, the liquid volumes in each tip 90 at the start and finish of the cycle are equal, i.e., the same amount of liquid is retained in the procedural steps represented by FIGS. 9 and 12. Accordingly, the pressure in the pipette cavities 14 is then at atmospheric at the completion of the cycle, and no single pipette tip 90 is fully emptied of the liquid 84.

The complete unit is then returned to the filling tray 50, the actuating device 48 is removed, and the contaminated pipetting device 32 and the filling tray, as well as all the remaining innoculating liquid 84, are discarded.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A process of using a multiple pipette sampler, said multiple pipette sampler comprising a plurality of pipettes, each of said pipettes including a narrow tip and a rim opposite said tip, said multiple pipette sampler further comprising a manifold above and in liquid communication with said pipettes, said multiple pipette sampler further comprising a means for varying the air pressure in said manifold;

said process comprising the steps of:

inserting said plurality of pipettes into a liquid retained within a filling tray while said manifold is in liquid communication with the atmosphere, thereby permitting capillary action to partially fill said pipettes with a uniform volume of said liquid;

decreasing the pressure in said manifold enough to draw said liquid upwards to a level above said rims of said pipettes, thereby effecting a complete wetting of interior portions of said pipettes, said liquid being retained at said level by the formation of stretched convexly shaped menisci;

increasing the air pressure in said manifold enough to allow said menisci to assume a concave shape, thereby retaining said pipettes in a completely liquid filled condition;

removing said plurality of pipettes from said filling tray and transferring said plurality of pipettes to receiving wells, said pipettes being placed below the level of liquid in said wells;

further increasing the air pressure in said manifold enough to dispense said liquid in pipettes into said receiving wells; and, removing said plurality of pipettes from said receiving panel whereby surface tension removes all but small uniform volumes of said liquid from said pipette tips, said uniform volumes being substantially equal to those present immediately after insertion of the pipettes into said filling tray.

2. A multiple pipette sampler, comprising:

a thin PVC plastic pipette sheet having an initial thickness between 0.015 and 0.020 inches;

a plurality of pipettes thermoformed in said pipette sheet and disposed in spaced parallel relation, said pipettes forming a uniform array extending perpendicularly from a bottom surface of said pipette sheet;

each of said pipettes forming a half hour-glass configuration having a larger diameter upper portion connected by a circular rim with said pipette sheet, each of said pipettes tapering to a small diameter tip portion forming a capillary tube for inducting a precise volume of sample liquid;

a concave housing thermoformed from a plastic sheet;

said housing having a top surface overlying an upper surface of said pipette sheet;

a plurality of concave depressions in said housing top surface, forming stiffening members engaging said upper surface of said pipette sheet, said stiffening members secured to said pipette sheet at intersticial zones between said pipettes;

said housing top surface connected to downwardly extending side wall portions;

a peripheral sealing edge formed in said side wall portions, said sealing edge extending in parallel engaging relation with a peripheral edge of said pipette sheet and secured thereto thereby forming a manifold in direct fluid communication with each of said pipettes; and a lower peripheral skirt portion of said housing extending downwardly from said sealing edge and partially surrounding said pipettes.

3. The multiple pipette sampler of claim 2, further comprising:

a filling tray thermoformed from a plastic sheet, said filling tray having upwardly extending side wall portions dimensioned for engagement with said housing skirt;

a plurality of vent notches at corner portions of said filling tray; and a plurality of concave liquid holding troughs formed in said tray, said troughs disposed to receive said pipettes when said housing is placed over said tray.

4. The multiple pipette sampler of claim 2, further comprising:

an aperture formed through said top surface of said housing, between said concave depressions; and a sealing washer surrounding said aperture in coaxial relation therewith, said washer secured to said housing top surface and including peripheral edge portions overlying at least two of said concave depressions.

5. The multiple pipette sampler of claim 4, further comprising:

a pressure actuator having a body including a piston slidably received in an internal cylinder;

a passage extending through a bottom end face of said actuator body and in fluid communication with said cylinder; and a sealing gasket secured on an end face of said bottom end face of said actuator body in coaxial relation with said passage, said sealing gasket dimensioned for engagement with said sealing washer on said housing top surface.

6. The multiple pipette sampler of claim 5, further comprising:

a pair of pivotal hook members pivotally mounted on said actuator body on opposite sides of said sealing gasket, said hook members including manually manipulable handle portions for engaging said hook members with said peripheral edge portion of said sealing washer, whereby said actuator passage may be placed in sealed fluid communication with said manifold.

7. The multiple pipette sampler of claim 6, further comprising:

a piston rod secured to said piston and extending upwardly through a top end face of said actuator body;

a transverse handle secured to an upper end of said piston rod;

a first adjustable threaded stop in said top end face of said actuator body disposed for abutment with said transverse handle;

an extended portion of said actuator body extending upwardly from said top end face;

a transverse flange on said extended portion overlying said transverse handle;

a second adjustable threaded stop in said transverse handle disposed for abutment with said transverse flange;

a first inclined cam surface formed on an extended edge of said handle;

a manually operable spring biased catch mounted for linear movement in said actuator body extended portion; and said catch having a second inclined cam surface configured to allow vertical movement of said handle above said catch and to prevent downward movement of said handle past said catch.

8. A multiple pipette sampler, comprising:

a thin PVC plastic pipette sheet having an initial thickness between 0.015 and 0.020 inches;

a plurality of pipettes thermoformed in said pipette sheet and disposed in spaced parallel relation, said pipettes forming a uniform array extending perpendicularly from a bottom surface of said pipette sheet;

each of said pipettes forming a half hour-glass configuration having a larger diameter upper portion connected by a circular rim with said pipette sheet, each of said pipettes tapering to a small diameter tip portion forming a capillary tube for inducting a precise volume of sample liquid;

a concave housing thermoformed from a plastic sheet;

said housing having a top surface overlying an upper surface of said pipette sheet;

a plurality of concave depressions in said housing top surface, forming stiffening members engaging said upper surface of said pipette sheet, said stiffening members secured to said pipette sheet at intersticial zones between said pipettes;

said housing top surface connected to downwardly extending side wall portions;

a peripheral sealing edge formed in said side wall portions, said sealing edge extending in parallel engaging relation with a peripheral edge of said pipette sheet and secured thereto, thereby forming a manifold in direct fluid communication with each of said pipettes;

a lower peripheral skirt portion of said housing extending downwardly from said sealing edge and partially surrounding said pipettes;

a filling tray thermoformed from a plastic sheet, said filling tray having upwardly extending side wall portions dimensioned for engagement with said housing skirt;

a plurality of vent notches at corner portions of said filling tray;

a plurality of concave liquid holding troughs formed in said tray, said troughs disposed to receive said pipettes when said housing is placed over said tray;

an aperture formed through said top surface of said housing, between said concave depressions;

a sealing washer surrounding said aperture in coaxial relation therewith, said washer secured to said housing top surface and including peripheral edge portions overlying at least two of said concave depressions;

a pressure actuator having a body including a piston slidably received in an internal cylinder;

a passage extending through a bottom end face of said actuator body and in fluid communication with said cylinder;

a sealing gasket secured on an end face of said bottom end face of said actuator body in coaxial relation with said passage, said sealing gasket dimensioned for engagement with said sealing washer on said housing top surface;

a pair of pivotal hook members pivotally mounted on said actuator body on opposite sides of said sealing gasket, said hook members including manually manipulable handle portions for engaging said hook members with said peripheral edge portions of said sealing washer, whereby said actuator passage may be placed in sealed fluid communication with said manifold;

a piston rod secured to said piston and extending upwardly through a top end face of said actuator body;

a transverse handle secured to an upper end of said piston rod;

a first adjustable threaded stop in said top end face of said actuator body disposed for abutment with said transverse handle;

an extended portion of said actuator body extending upwardly from said top end face;

transverse flange on said extended portion overlying said transverse handle;

a second adjustable threaded stop in said transverse handle disposed for abutment with said transverse flange;

a first inclined cam surface formed on an extended edge of said handle;

a manually operable spring biased catch mounted for linear movement in said actuator body extended portion; and said catch having a second inclined cam surface configured to allow vertical movement of said handle above said catch and to prevent downward movement of said handle past said catch.

9. A multiple pipette sampler, comprising:

a plurality of pipettes formed in a thin sheet, thereby forming a pipette sheet, each of said pipettes terminating in a narrow tip, each of said pipettes having a rim proximate said thin sheet and opposite said tip, said pipettes being thermoformed in said thin sheet;

a housing sealingly attachable to said pipette sheet, said attachment of said housing to said sheet forming a manifold in fluid communication with each of said pipettes;

pressure varying means operably attachable to said manifold, said pressure varying means alternatively permitting an evacuation and pressurization of said manifold; and strengthening means whereby said attached pipette sheet and housing form a rigid monocoque structure, thereby permitting the transmission of shear forces and stresses without deformation of a planar orientation of said pipette sheet.

10. The multiple pipette sampler of claim 9, wherein said manifold includes an attachment means whereby said pressure varying means may be joined physically as well as pneumatically to said manifold, thereby allowing said pipette sheet, said housing, and said pressure varying device to be easily transported together during usage of said pipette sampler.

11. The multiple pipette sampler of claim 9, wherein a film of hydrophobic plastic surrounds said rim of each of said pipettes.

12. A multiple pipette sampler, comprising:
   a plurality of pipettes formed in a thin sheet, thereby forming a pipette sheet, each of said pipettes terminating in a narrow tip, each of said pipettes having a rim proximate said thin sheet and opposite said tip, said pipettes being thermoformed in said thin sheet;
   a housing sealingly attachable to said pipette sheet, said attachment of said housing to said sheet forming a manifold in fluid communication with each of said pipettes;
   pressure varying means operably attachable to said manifold, said pressure varying means alternatively permitting an evacuation and pressurization of said manifold; and
   said pipette sheet attached to said housing by a dielectric heating process.

13. The multiple pipette sampler of claim 12, wherein said manifold includes an attachment means whereby said pressure varying means may be joined physically as well as pneumatically to said manifold, thereby allowing said pipette sheet, said housing, and said pressure varying device to be easily transported together during usage of said pipette sampler.

14. The multiple pipette sampler of claim 12, wherein a film of hydrophobic plastic surrounds said rim of each of said pipettes.

15. A multiple pipette sampler, comprising:
   a plurality of pipettes formed in a thin sheet, thereby forming a pipette sheet, each of said pipettes terminating in a narrow tip, each of said pipettes having a rim proximate said thin sheet and opposite said tip, said pipettes being thermoformed in said thin sheet;
   a housing sealingly attachable to said pipette sheet, said attachment of said housing to said sheet forming a manifold in fluid communication with each of said pipettes;
   pressure varying means operably attachable to said manifold, said pressure varying means alternatively permitting an evacuation and pressurization of said manifold; and
   each of said pipettes shaped like the upper half of an hour glass, each of said pipettes having a narrow stem and a wider body, said narrow stems functioning as capillary tubes, said capillarity permitting a substantial identity between an initial partially filled volume and a final volume remaining in each of said pipettes after usage of said pipettes.

16. The multiple pipette sampler of claim 15, wherein said manifold includes an attachment means whereby said pressure varying means may be joined physically as well as pneumatically to said manifold, thereby allowing said pipette sheet, said housing, and said pressure varying device to be easily transported together during usage of said pipette sampler.

17. The multiple pipette sampler of claim 15, wherein a film of hydrophobic plastic surrounds said rim of each of said pipettes.

18. A multiple pipette sampler, comprising:
   a thin plastic pipette sheet;
   a plurality of pipettes formed in said pipette sheet and disposed in spaced parallel relation, said pipettes extending generally perpendicularly from a bottom surface of said pipette sheet;
   each of said pipettes forming a half hour-glass configuration having a larger diameter upper portion connected by a circular rim with said pipette sheet, each of said pipettes tapering to a small diameter tip portion forming a capillary tube for inducting a precise volume of sample liquid;
   a concave housing;
   said housing having a top surface overlying an upper surface of said pipette sheet;
   a plurality of concave depressions in said housing top surface, forming stiffening members engaging said upper surface of said pipette sheet, said stiffening members secured to said pipette sheet at intersticial zones between said pipettes;
   said housing top surface connected to downwardly extending side wall portions; and
   a peripheral sealing edge formed in said side wall portions, said sealing edge extending in sealing relation with a peripheral edge of said pipette sheet and secured thereto, thereby forming a manifold in direct fluid communication with each of said pipettes.

19. The multiple pipette sampler of claim 18, further comprising:
   a filling tray formed from a plastic sheet, said filling tray having upwardly extending side wall portions dimensioned for engagement with said housing skirt;
   a plurality of vent notches at corner portions of said filling tray; and
   a plurality of concave liquid holding troughs formed in said tray, said troughs disposed to receive said pipettes when said housing is placed over said tray.

20. The multiple pipette sampler of claim 18, further comprising:
   an aperture formed through said top surface of said housing, between said concave depressions; and
   a sealing washer surrounding said aperture in coaxial relation therewith, said washer secured to said housing top surface and including peripheral edge portions overlying at least two of said concave depressions.

21. The multiple pipette sampler of claim 20, further comprising:
   a pressure actuator having a body including a piston slidably received in an internal cylinder;
   a passage extending through a bottom end face of said actuator body and in fluid communication with said cylinder; and
   a sealing gasket secured on an end face of said bottom end face of said actuator body in coaxial relation with said passage, said sealing gasket dimensioned for engagement with said sealing washer on said housing top surface.

22. The multiple pipette sampler of claim 18, wherein said manifold includes an attachment means whereby said pressure varying means may be joined physically as well as pneumatically to said manifold, thereby allowing said pipette sheet, said housing, and said pressure varying device to be easily transported together during usage of said pipette sampler.

23. The multiple pipette sampler of claim 18, wherein a film of hydrophobic plastic surrounds said rim of each of said pipettes.

* * * * *